(12) United States Patent
Kurihara

(10) Patent No.: US 11,744,304 B2
(45) Date of Patent: Sep. 5, 2023

(54) UNDERARM SWEAT PAD

(71) Applicant: DAIO PAPER CORPORATION, Shikokuchuo (JP)

(72) Inventor: Ryoko Kurihara, Sakura (JP)

(73) Assignee: DAIO PAPER CORPORATION, Shikokuchuo (JP)

( * ) Notice: Subject to any disclaimer, the term of this patent is extended or adjusted under 35 U.S.C. 154(b) by 229 days.

(21) Appl. No.: 17/262,427

(22) PCT Filed: Aug. 28, 2019

(86) PCT No.: PCT/JP2019/033668
§ 371 (c)(1),
(2) Date: Jan. 22, 2021

(87) PCT Pub. No.: WO2020/045484
PCT Pub. Date: Mar. 5, 2020

(65) Prior Publication Data
US 2021/0289863 A1  Sep. 23, 2021

(30) Foreign Application Priority Data
Aug. 29, 2018  (JP) .................. 2018-160286

(51) Int. Cl.
*A41D 27/13* (2006.01)
(52) U.S. Cl.
CPC .................. *A41D 27/133* (2013.01)
(58) Field of Classification Search
CPC .............. A41D 27/133; A41D 27/13
See application file for complete search history.

(56) References Cited

U.S. PATENT DOCUMENTS 3,345,643 A * 10/1967 Bradley ............... A41D 27/13
428/140
4,059,114 A * 11/1977 Richards .......... A61F 13/51305
604/366

(Continued)

FOREIGN PATENT DOCUMENTS

CN        101861103 A        10/2010
EP          3437612 A1 *      2/2019  ........ A61F 13/15617

(Continued)

OTHER PUBLICATIONS

Translation of International Search Report dated Nov. 26, 2019 and Written Opinion of corresponding application No. PCT/JP2019/033668; 8 pgs.

(Continued)

*Primary Examiner* — Alissa L Hoey
(74) *Attorney, Agent, or Firm* — Maier & Maier, PLLC

(57) ABSTRACT

To configure a pad so as to be gentle to the skin, to prevent stretching and/or tearing of the front surface sheet, and to not reduce liquid permeability and air permeability. [Solution] An underarm sweat pad in which an absorbent is interposed between a front surface sheet and a back surface sheet and which is used folded in two at a folding line and attached to the inside of the axillary portion of a garment. The front surface sheet is composed of a hydrophilic cellulose fiber. Adhesive regions, in which an adhesive for bonding the front surface sheet to the absorbent is applied, are formed as stripes that are parallel to the folding line and are spaced at intervals in the direction that is orthogonal to the folding line.

20 Claims, 6 Drawing Sheets

(56) References Cited

U.S. PATENT DOCUMENTS

| | | | | |
|---|---|---|---|---|
| 4,485,492 | A * | 12/1984 | Sneider | A41D 27/132/56 |
| 4,773,905 | A * | 9/1988 | Molee | A61F 13/4758 D24/126 |
| 5,103,500 | A * | 4/1992 | Nager | A41D 27/13 604/360 |
| 5,864,889 | A * | 2/1999 | Suffern | A41D 27/10 2/54 |
| 6,563,013 | B1 * | 5/2003 | Murota | A61F 13/533 604/385.01 |
| 7,367,966 | B2 * | 5/2008 | Mizutani | A61F 15/001 604/385.03 |
| 7,388,123 | B2 * | 6/2008 | Cowell | A61F 13/51113 604/382 |
| 7,736,349 | B2 * | 6/2010 | Gagliardi | A61F 13/53 604/385.01 |
| 7,954,170 | B2 * | 6/2011 | Hofer | A41D 27/13 2/53 |
| 8,251,965 | B2 * | 8/2012 | Costea | A61F 13/51394 604/385.01 |
| 8,496,775 | B2 * | 7/2013 | Deng | B05C 5/0254 156/292 |
| 10,071,000 | B2 * | 9/2018 | Umemoto | A61F 13/51108 |
| 10,195,090 | B2 * | 2/2019 | Kurihara | A61F 13/536 |
| 10,327,480 | B2 * | 6/2019 | Khan | A61F 13/47 |
| 10,555,843 | B2 * | 2/2020 | Suzuki | A61F 13/4758 |
| 10,806,642 | B2 * | 10/2020 | Tagomori | A61F 13/4756 |
| 11,202,724 | B2 * | 12/2021 | Nagashima | A61F 13/51121 |
| 11,207,220 | B2 * | 12/2021 | Rosati | A61F 13/535 |
| 11,412,795 | B2 * | 8/2022 | Jones | A41D 27/133 |
| 11,484,070 | B2 * | 11/2022 | Hunt | A41C 3/04 |
| 2006/0150294 | A1 * | 7/2006 | Yanamadala | A41D 27/13 2/53 |
| 2006/0224133 | A1 * | 10/2006 | Gannon | A61F 13/82 604/385.03 |
| 2011/0179544 | A1 * | 7/2011 | Courvoisier | A41D 27/13 2/53 |
| 2013/0165889 | A1 * | 6/2013 | Kawakami | A61F 13/532 604/385.04 |
| 2018/0279702 | A1 * | 10/2018 | Karbakhsh | A41D 27/133 |
| 2019/0053958 | A1 * | 2/2019 | Kurihara | A61F 13/51113 |
| 2019/0060139 | A1 * | 2/2019 | Nagashima | A61F 13/51108 |

FOREIGN PATENT DOCUMENTS

| | | |
|---|---|---|
| JP | S6154816 U | 4/1986 |
| JP | H0311017 U | 2/1991 |
| JP | 2006-280683 A | 10/2006 |
| JP | 2009-121001 A | 6/2009 |
| JP | 2017-176315 A | 10/2017 |
| JP | 201894301 A | 6/2018 |
| WO | WO-2016147014 A1 * | 9/2016 |

OTHER PUBLICATIONS

Office Action dated May 23, 2022, in connection with corresponding Chinese Application No. 201980049122.0 (18 pp., including machine-generated English translation).

* cited by examiner

UNDERARM SWEAT PAD

FIELD

The present disclosure relates to an underarm sweat pad used by being attached to an inside of an axillary portion of a garment.

BACKGROUND

Conventionally, as the underarm sweat pad, there has been known an underarm sweat pad in which an absorbent body that absorbs sweat is interposed between a liquid-impermeable back surface sheet made of a polyethylene sheet, a polyethylene sheet laminated nonwoven fabric, etc. and a liquid-permeable front surface sheet made of a non-woven fabric, a porous plastic sheet, etc.

In a disposable underarm sweat pad, as the front surface sheet, a nonwoven fabric which is a man-made fiber is widely adopted since the strength is high, and stretching or tearing due to rubbing rarely occurs. However, the front surface sheet made of the man-made fiber has a problem of causing itching, rashes, etc., and does not meet needs of people who are particular about 100% cotton clothing since they have sensitive skin. On the other hand, there is a pad made of 100% cotton that can be washed and used many times. However, there is a problem that washing is troublesome.

In a case where a cotton nonwoven fabric made of 100% cotton is used as the front surface sheet of the underarm sweat pad, since the cotton nonwoven fabric has a weaker strength than that of the nonwoven fabric made of the man-made fiber, there is a problem that stretching or tearing easily occurs by rubbing. An occurrence mechanism of stretching or tearing by rubbing of the front surface sheet is that bonding between the front surface sheet and the absorbent body is released due to movement during wearing, so that the front surface sheet floats from the absorbent body, and a front surface sheet part floating from the absorbent body rubs against a skin surface to cause stretching or tearing.

An example of an underarm sweat pad using a cotton fiber as a material of a front surface sheet is disclosed in Patent Document 1, etc. below. In addition, Patent Document 2 below discloses an absorbent article in which a spun lace nonwoven fabric made of 100% by weight of cotton fibers is used as a front surface sheet, and the front surface sheet is bonded to an absorbent body side by a plurality of adhesive parts extending along a longitudinal direction and spaced in a width direction and compression grooves formed close to the adhesive parts and recessed from an outer surface side of the front surface sheet toward the absorbent body.

Patent Document 1: JP-A-2009-121001
Patent Document 2: JP-A-2017-176315

SUMMARY

However, the above-mentioned Patent Document 1 fails to describe in detail a method of bonding the front surface sheet and the absorbent body together. Further, in a case where a bonding strength between the front surface sheet and the absorbent body is insufficient, there is concern that stretching or tearing may occur when the front surface sheet rubs against the skin surface and peels off from the absorbent body.

In addition, the above-mentioned Patent Document 2 describes that the front surface sheet is bonded to the absorbent body side by the adhesive parts based on an adhesive and the compression grooves. However, this bonding is for rapidly permeating water absorbed in the front surface sheet into the absorbent body. When this scheme is used for the underarm sweat pad, it is not sufficiently satisfactory to prevent the front surface sheet from peeling off from the absorbent body due to rubbing against the skin surface.

To prevent peeling of the front surface sheet, there is a method of attaching the entire surface of the front surface sheet to the absorbent body using an adhesive. However, when the adhesive is applied to the entire surface, a body fluid hardly moves from the front surface sheet to the absorbent body, and there is a problem that air permeability is lowered.

Therefore, a main problem of the invention is to provide an underarm sweat pad that is gentle to skin, prevents stretching or tearing of a front surface sheet, and does not lower liquid permeability and air permeability.

To solve the above problem, there is provided an underarm sweat pad, an absorbent body being interposed between a liquid-permeable front surface sheet and a liquid-impermeable back surface sheet, the underarm sweat pad being attached to an inner side of an axillary portion of a garment and used while being bent in two parts at a folding line, characterized in that the front surface sheet is made of a hydrophilic cellulosic fiber, and adhesive regions in which an adhesive for bonding the front surface sheet to the absorbent body are formed as stripes that are parallel to the folding line and are spaced at intervals in a direction orthogonal to the folding line, and debossed grooves recessed to a non-skin side are formed along a direction in which the adhesive regions extend on a skin-side surface of the front surface sheet overlapping each of the adhesive regions.

In the invention, the front surface sheet is made of the hydrophilic cellulosic fiber such as cotton fiber, and thus is gentle to skin, hardly causes itching, rashes, etc., and can meet needs of people who are particular about 100% cotton clothing since they have sensitive skin.

In addition, since the front surface sheet is firmly bonded to the absorbent body by the adhesive regions and the debossed grooves, the front surface sheet hardly peels off from the absorbent body, and it is possible to prevent the front surface sheet from floating from the absorbent body to cause stretching or tearing.

In addition, since the adhesive regions are formed as stripes with an interval therebetween, liquid permeability and air permeability can be sufficiently ensured in a separated portion between the adhesive regions.

In the invention, there is provided the underarm sweat pad, in which the adhesive region is formed along the folding line at a position overlapping the folding line, and a plurality of adhesive regions is formed to be parallel to the folding line at intervals using the folding line as a reference line in each of regions on both sides of the folding line.

In the invention, since the plurality of adhesive regions is formed at intervals in each of the regions on both sides of the folding line using the position of the folding line as a reference line, peeling of the front surface sheet at the position of the folding line can be reliably prevented, liquid permeability to the absorbent body is not hindered, and air permeability can be sufficiently ensured.

As the invention, there is provided the underarm sweat pad, in which a width of the adhesive region is formed to be 2 to 5 times a groove width of a debossed groove overlapping the adhesive region.

In the invention, since the width of the adhesive region is formed to be larger than the groove width of the debossed groove at a predetermined ratio, the debossed groove can be reliably formed at a position overlapping the adhesive region, and it is possible to maintain a state in which the front surface sheet is firmly bonded to the absorbent body by the adhesive regions and the debossed grooves.

In the invention, there is provided the underarm sweat pad, in which an interval between adjacent adhesive regions is 0.8 to 1.5 times the width of the adhesive region.

In the invention, by forming the interval between the adjacent adhesive regions at a predetermined ratio with respect to the width of the adhesive region, it is possible to prevent the liquid permeability from decreasing due to the adhesive regions, ensure the bonding strength between the front surface sheet and the absorbent body, and reliably prevent peeling of the front surface sheet.

As the invention, there is provided the underarm sweat pad, in which one of the debossed grooves is formed in a linear shape along the folding line at a position of the folding line.

In the invention, one of a plurality of debossed grooves is formed in a linear shape along the folding line at a position of the folding line. In this way, the underarm sweat pad is easily bent at the folding line.

As the invention, there is provided the underarm sweat pad, in which the debossed grooves formed in the regions on both sides of the folding line are formed in a straight line shape or a wavy shape in which concaves and convexes are repeated within a width of the adhesive region.

In the invention, by forming the debossed grooves formed in a region other than the region overlapping the folding line in various forms, it is possible to attempt firm fixing to the absorbent body.

As the invention, there is provided the underarm sweat pad, in which the debossed grooves extend in a direction substantially coinciding with a fiber orientation direction of the front surface sheet.

In the invention, by making the direction in which the debossed grooves extend substantially coincide with the fiber orientation direction of the front surface sheet, it is possible to prevent tearing of the front surface sheet by the strength of the front surface sheet with respect to the fiber orientation direction when rubbing against the skin surface occurs in a direction parallel to the direction in which the debossed grooves extend. Further, when rubbing against the skin surface occurs in a direction orthogonal to the direction in which the debossed grooves extend, even though the strength of the front surface sheet is weak in a direction orthogonal to the fiber orientation direction, since the front surface sheet is constrained by the adhesive regions and the debossed grooves so that a moving distance is limited, it is possible to prevent tearing of the front surface sheet.

As the invention, there is provided the underarm sweat pad, in which the adhesive is not applied to a region other than the adhesive regions, or is applied to the region with a lower basis weight than a basis weight of the adhesive applied to the adhesive regions.

As the invention, there is provided the underarm sweat pad, in which the basis weight of the adhesive applied to the region other than the adhesive regions is 0 to 0.5 times the basis weight of the adhesive applied to the adhesive regions.

In the invention, since the adhesive is not applied to the region other than the adhesive regions, or is applied to the region with a predetermined basis weight or less, it is possible to ensure liquid permeability and air permeability, and to improve the bonding strength of the front surface sheet.

As described above in detail, according to the invention, it is possible to provide an underarm sweat pad that is gentle to skin, prevents stretching or tearing of a front surface sheet, and does not lower liquid permeability and air permeability.

DETAILED DESCRIPTION

Hereinafter, embodiments of the invention will be described in detail with reference to the drawings.

Figure 1:
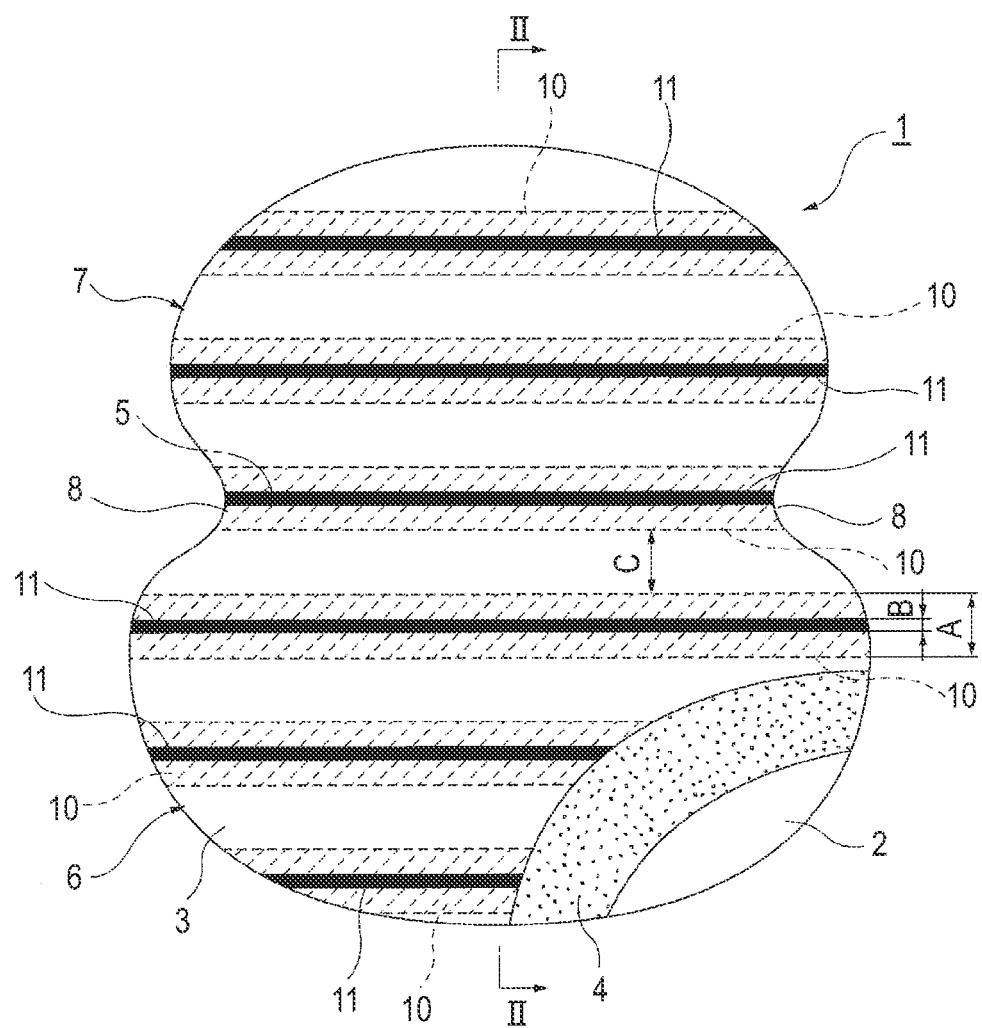
FIG. 1 is a partially broken development diagram of an underarm sweat pad 1 according to the invention.
Figure 2:
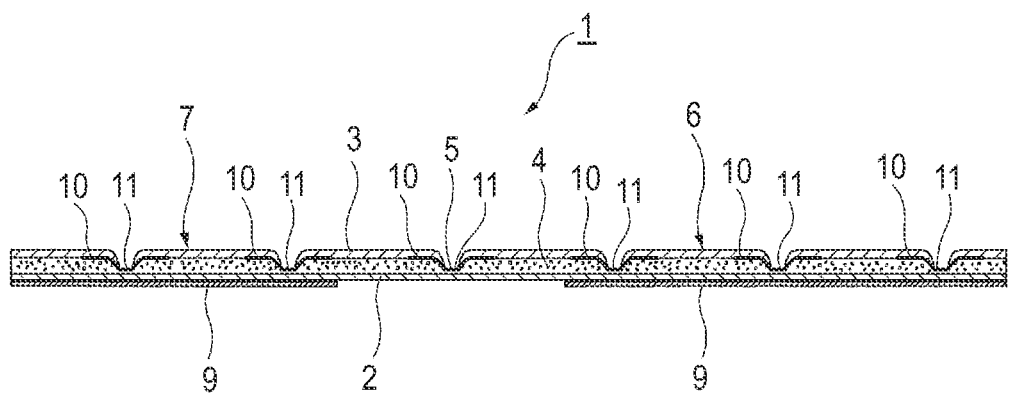
FIG. 2 is a diagram taken along the line II-II of FIG. 1.

[Basic configuration of underarm sweat pad 1] As illustrated in FIGS. 1 and 2, an underarm sweat pad 1 according to the invention includes a liquid-impermeable back surface sheet 2 made of a polyethylene sheet, a polypropylene sheet, etc., a liquid-permeable front surface sheet 3 made of natural fiber, and an absorbent body 4 interposed between both the sheets 2 and 3 to absorb sweat. It is possible to adopt a structure in which the back surface sheet 2, the front surface sheet 3, and the absorbent body 4 are formed to have substantially the same size, and respective layers are bonded by bonding means such as an adhesive, or a structure in which outer edge portions of the back surface sheet 2 and the front surface sheet 3 extending outside the absorbent body 4 are bonded by bonding means around the absorbent body 4.

The underarm sweat pad 1 is used by being attached to an inside of an axillary portion of a garment, and is worn with the front surface sheet 3 facing a skin side and the back surface sheet 2 facing a garment side.

The underarm sweat pad 1 is attached to the garment in a state of being bent in two parts along a predetermined folding line 5. At the time of being attached to the garment, the folding line 5 is disposed to substantially follow a suture line of a peripheral edge of an armhole provided at a boundary between a torso and a sleeve of the garment, and both sides of the folding line 5 form a torso-side region 6 disposed on a torso side of the garment and a sleeve-side region 7 disposed on a sleeve side of the garment, respectively. The torso-side region 6 is formed to have a larger area than that of the sleeve-side region 7, so that more sweat can be absorbed. In the underarm sweat pad 1 illustrated in FIG. 1, the sleeve-side region 7 is formed on an upper side of the folding line 5, and the torso-side region 6 is disposed on a lower side of the folding line 5. It is preferable to form constricted portions 8 recessed inward on outlines at both ends of the folding line 5.

In a planar shape of the underarm sweat pad 1, as illustrated in FIG. 1, a pair of left and right constricted portions 8 is formed in a middle part of left and right outlines. The constricted portions 8 are formed by a smooth concave curve recessed inward at a boundary portion between the torso-side region 6 and the sleeve-side region 7. In this way, the underarm sweat pad 1 has a substantially gourd-shaped planar shape. The folding line 5 is provided at a position connecting apexes of concave curves in the left and right constricted portions 8 and 8. The outlines of the torso-side region 6 and the sleeve-side region 7 may be formed by a smooth curve such as an arc or an elliptic arc as illustrated in the drawing, or may be formed by a shape including a plurality of concaves and convexes.

Hereinafter, a structure of the underarm sweat pad 1 will be further described in detail.

For the back surface sheet 2, a sheet material having at least a water-blocking property such as an olefin-based resin sheet such as polyethylene or polypropylene is used. In addition to this material, it is possible to use a laminated nonwoven fabric obtained by laminating a nonwoven fabric on a polyethylene sheet, etc., or a nonwoven fabric sheet (in which case, a water-blocking film and a nonwoven fabric are included in a liquid-impermeable back surface sheet), etc. after the water-blocking film is interposed to ensure substantially liquid impermeability. Even though a non-moisture permeable material may be used, a moisture permeable material is preferable from a viewpoint of preventing stuffiness. This water-blocking and moisture-permeable sheet material is a microporous sheet obtained by melt kneading an inorganic filler in an olefin-based resin such as polyethylene or polypropylene to form a sheet, and then monoaxially or biaxially stretching the sheet. A polyethylene film is particularly preferable, and beige or a similar color is preferably used to make the sheet inconspicuous.

Next, the front surface sheet 3 includes a nonwoven fabric made of a hydrophilic cellulosic fiber that is not heat-sealed. Examples of the hydrophilic cellulosic fiber include a naturally derived fiber such as a cotton fiber or a pulp fiber, and an artificial cellulosic fiber such as a rayon fiber, an acetate fiber, or a lyocell fiber. As the cotton fiber, it is possible to use all cotton fibers such as raw cotton of arboreous cotton, a refined and bleached cotton fiber, a cotton fiber subjected to dyeing after being refined and bleached, a refined and bleached absorbent cotton fiber, and wool defibrated from yarn or cloth. However, to enhance an absorption speed and diffusibility of a liquid in the front surface sheet 3, it is particularly preferable to use absorbent cotton obtained by defatting the natural fat and oil of cotton wax attached to a surface of the cotton fiber.

In particular, when the naturally derived fiber is used as the front surface sheet 3, it is preferable to use a nonwoven fabric made of 100% by weight of cotton fiber, which has high water absorption performance and excellent diffusibility, rather than paper made of pulp fibers, etc. Being made of 100% by weight of cotton fiber means that the cotton fiber is used alone and no chemical fiber is included. In this way, an absorption speed at which the front surface sheet 3 absorbs liquid is increased, and the diffusibility is improved.

There is no limitation on a method of processing the nonwoven fabric of the front surface sheet 3. However, to prevent the absorbent body 4 from falling off, it is preferable to use a processing method such as a spun bond method, a melt blown method, or a needle punch method in which the fiber density of an obtained product is increased. In particular, it is preferable to use a spun lace method to enhance the body fluid absorption speed and the diffusibility in the front surface sheet 3. The spun lace nonwoven fabric has advantages such as not using an adhesive and having flexibility.

The basis weight of the front surface sheet 3 is set to 10 to 50 g/m², preferably 15 to 35 g/m², and the thickness is set to 0.3 to 0.7 mm, preferably 0.4 to 0.5 mm. The basis weight is calculated by measuring the weight of 5 cm×30 cm×10 sheets using an electronic balance and converting the weight into square meters. The thickness is obtained according to JIS L1913.

In the underarm sweat pad 1, the front surface sheet 3 includes a nonwoven fabric made of a hydrophilic cellulosic fiber, and thus is gentle to skin, hardly causes itching, rashes, etc., and can meet needs of people who are particular about 100% cotton clothing since they have sensitive skin.

As the absorbent body 4 interposed between the back surface sheet 2 and the front surface sheet 3, a known one can be used as long as it has a property of absorbing and retaining sweat. For example, it is possible to include pulp, superabsorbent resin, etc. In addition, chemical fibers may be mixed in the pulp. Examples of the pulp include chemical pulp obtained from wood, cellulose fibers such as molten pulp, and those containing artificial cellulose fibers such as rayon and acetate, and softwood pulp having a longer fiber length is more preferably used than hardwood pulp in terms of function and cost. As the absorbent body 4, a fiber stack may be used, and it is preferable to use an air-laid absorbent body that can reduce the bulk. The air-laid absorbent body may be a nonwoven fabric only including pulp or a nonwoven fabric including pulp and polymer, and another binder may be included. In addition, it is possible to use a polymer sheet obtained by disposing a superabsorbent resin between two nonwoven fabric layers. The basis weight of the absorbent body 4 is preferably 50 to 150 g/m². The absorbent body 4 may be surrounded by a wrapping sheet made of crepe paper or a nonwoven fabric to maintain a shape, rapidly diffuse sweat, and prevent reversion of absorbed sweat.

As illustrated in FIG. 2, on an outer surface side (non-skin surface side) of the back surface sheet 2, for fixing to the garment, an anti-slip adhesive layer 9 is provided by an appropriate application pattern.

[Bonding Structure of Front Surface Sheet 3 and Absorbent Body 4]

Next, a description will be given of a bonding structure for bonding the front surface sheet 3 to the absorbent body 4. In the underarm sweat pad 1, the adhesive regions 10, in which an adhesive for bonding the front surface sheet 3 to the absorbent body 4, are formed as stripes that are parallel to the folding line 5 and space at intervals in a direction orthogonal to the folding line 5. In addition, on the skin-side surface of the front surface sheet 3 overlapping each adhesive region 10, debossed grooves 11 recessed to the non-skin side are formed along a direction in which the adhesive regions 10 extend. The front surface sheet 3 is firmly bonded to the absorbent body 4 by the adhesive regions 10 and the debossed grooves 11.

The adhesive regions 10 include adhesive layers arranged between the front surface sheet 3 and the absorbent body 4. It is preferable to use a hot melt adhesive as an adhesive included in the adhesive layers. Each of the adhesive regions 10 is formed as a band having a predetermined width extending along a direction parallel to the folding line 5, and a plurality of the adhesive regions 10 is disposed at intervals in a direction substantially orthogonal to the folding line 5. Both end edges of the adhesive region 10 extend to the left and right outlines of the underarm sweat pad 1, and the adhesive regions 10 are formed over the entire width of the underarm sweat pad 1.

It is desirable that the adhesive region 10 is formed along the folding line 5 at a position overlapping the folding line 5, and a plurality of adhesive regions 10 is formed at intervals using the folding line 5 as a reference line in respective regions (the torso-side region 6 and the sleeve-side region 7) on both sides of the folding line 5 in parallel with the folding line 5. In this way, by providing the adhesive region 10 at the position overlapping the folding line 5 for bending the underarm sweat pad 1 in two parts during wearing, it is possible to prevent the front surface sheet 3 from peeling off from the absorbent body 4 at the folding line 5, and to prevent tearing, etc. of the front surface sheet 3 at the folding line 5.

The debossed grooves 11 are groove portions in which at least the front surface sheet 3 and the absorbent body 4 are integrally recessed to the non-skin side by compression from the skin-contact surface side of the front surface sheet 3 at positions overlapping the adhesive regions 10. One or a plurality of debossed grooves 11 can be formed in each of the adhesive regions 10. The debossed grooves 11 extend along the direction in which the adhesive regions 10 extend.

It is desirable that the debossed groove 11 is formed along the folding line 5 at a position of the folding line 5. In this way, it is easy to bend the underarm sweat pad 1 along the folding line 5 using the debossed groove 11 as a flexible shaft.

In the underarm sweat pad 1, since the front surface sheet 3 is firmly bonded to the absorbent body 4 by the adhesive regions 10 and the debossed groove 11, the front surface sheet 3 hardly peels off from the absorbent body 4, and it is possible to prevent the front surface sheet 3 from floating from the absorbent body 4 to cause stretching or tearing.

In addition, since the adhesive regions 10 are formed as stripes with an interval therebetween, liquid permeability and air permeability can be sufficiently ensured in a separated portion between the adhesive regions 10 and 10.

Next, dimensions of the respective portions will be described. As illustrated in FIG. 1, a groove width B of the debossed grooves 11 is preferably 1 to 3 mm. When the groove width is thinner than the above range, there is concern that the material may break when the debossed grooves 11 are compressed. When the groove width is thicker than the above range, the debossed grooves 11 are hard and it is easy to feel uncomfortable.

In addition, a width A of the adhesive regions 10 is preferably formed wider than the groove width B of the debossed grooves 11 overlapping the adhesive regions 10. Specifically, the width A of the adhesives regions 10 is preferably formed to be 2 to 5 times as wide as the groove width B of the debossed grooves 11 overlapping the adhesive regions 10 (A=2B to 5B). When the adhesive regions 10 are formed to have such a width A, the debossed grooves 11 can be reliably formed at positions overlapping the adhesive regions 10, and it is possible to maintain a state in which the front surface sheet 3 is firmly bonded to the absorbent body 4 by the adhesive regions 10 and the debossed grooves 11.

Arrangement positions of the debossed grooves 11 formed to overlap the respective adhesive regions 10 are arbitrary. However, it is desirable to dispose the debossed groove 11 in a central portion with respect to the width A of the adhesive region 10 in terms of enhancing the bonding strength of the adhesive region 10 and the debossed groove 11 since the adhesive region extends on both sides of the debossed groove 11 with a substantially uniform width so that the bonding strength is substantially uniform on both sides of the debossed groove 11.

An interval C between the adjacent adhesive regions 10 and 10 is preferably 0.8 to 1.5 times the width A of the adhesive region 10 (C=0.8A to 1.5A). When the interval C is narrower than this value, there is concern that the adhesive may hinder movement of the body fluid from the surface to the absorbent body 4. When the interval C is wider than this value, a non-bonded region between the front surface sheet 3 and the absorbent body 4 becomes large, so that the front surface sheet 3 is easily stretched or torn by rubbing against the skin.

Next, a description will be given of an arrangement pattern of the debossed grooves 11. In the embodiment illustrated in FIG. 1, the debossed grooves 11 are disposed at the position of the folding line 5, and disposed at substantially equal intervals in each of the torso-side region 6 and the sleeve-side region 7 on both sides using the debossed groove 11 disposed at the folding line position as a reference line. In the embodiment illustrated in FIG. 1, all the debossed grooves 11 are formed as continuous straight lines compressed with a substantially constant pressure (depth).

Figure 3:
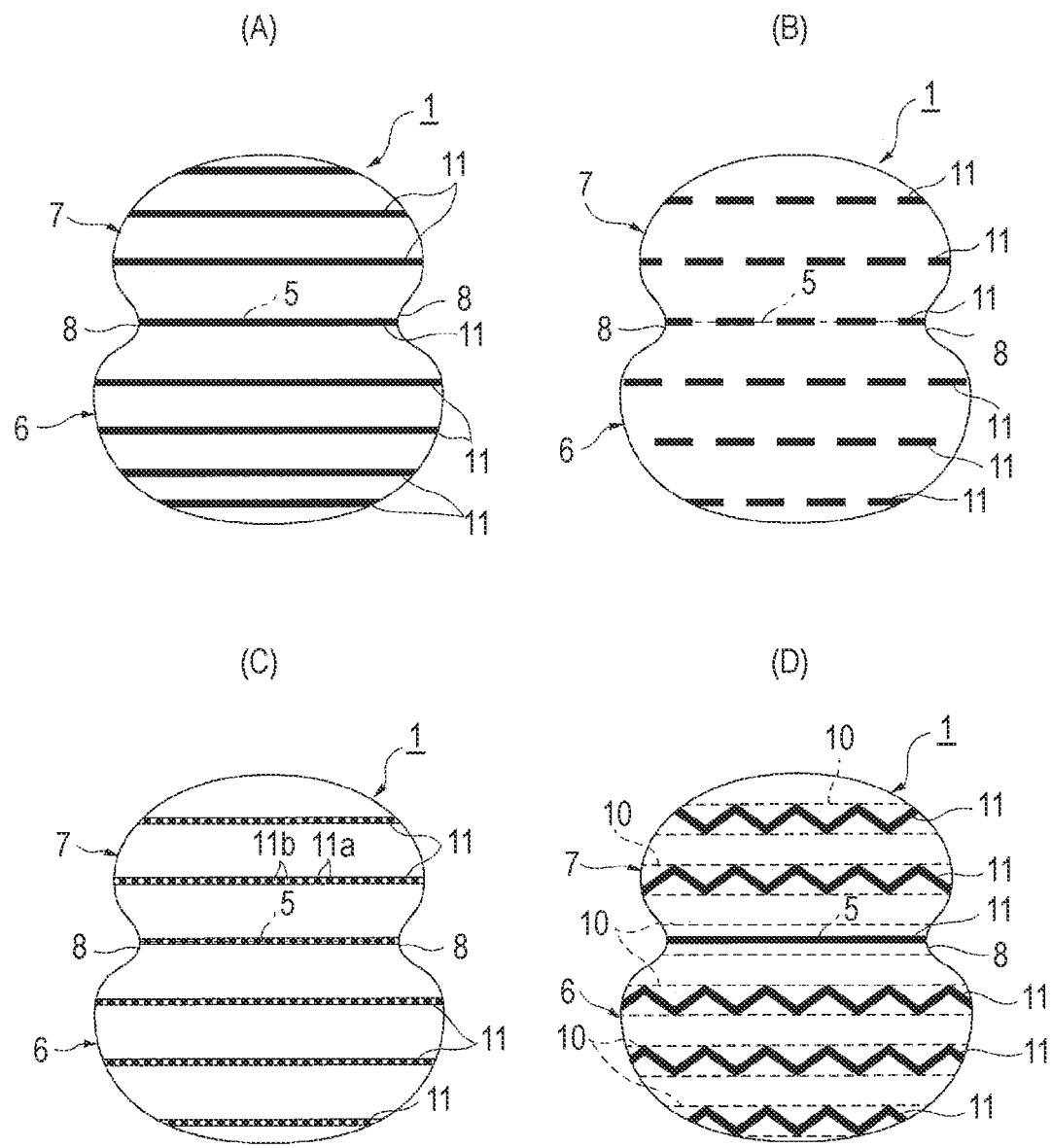
FIG. 3 is a plan view of the underarm sweat pad 1 illustrating a pattern of debossed grooves 11.

As a modification of the arrangement pattern of the debossed grooves 11, as illustrated in FIG. 3(A), the debossed grooves 11 may not be arranged at equal intervals and may be formed at unequal intervals. In the illustrated example, arrangement intervals become narrower as a distance from the folding line 5 increases. However, conversely, the arrangement intervals may become wider as the distance from the folding line 5 increases.

Alternatively, the debossed grooves 11 may not be continuous lines and may be formed as discontinuous lines in which compressed portion and non-compressed portion are alternately disposed along the direction in which the debossed grooves extend as illustrated in FIG. 3(B). In this case, a length of the compressed portion is preferably longer than a length of the non-compressed portion. In addition, from a viewpoint of not lowering the bonding strength, it is preferable to dispose adjacent debossed grooves 11 and 11 so that non-compressed portions do not overlap in a direction orthogonal to the debossed grooves 11.

As illustrated in FIG. 3(C), the debossed grooves 11 may be formed in a pattern having a high-compressed portion 11a and a low-compressed portion 11b. In the illustrated example, a portion interposed between straight lines on both sides is the debossed groove 11. In the debossed groove 11, portions are high-compressed portions 11a, and the other portions are low-compressed portion 11b. By partially providing the high-compressed portions 11a, the bonding strength of the front surface sheet 3 by the debossed grooves 11 can be further increased.

Alternatively, as illustrated in FIG. 3(D), the debossed groove 11 may be formed in a wavy shape in which concaves and convexes are repeated within the width of the adhesive region 10. In this way, a bonding length by the debossed groove 11 between the front surface sheet 3 and the absorbent body 4 becomes long, and the bonding strength therebetween can be further increased. However, the debossed groove 11 formed at the position of the folding line 5 is preferably formed in a linear shape so that the underarm sweat pad 1 is easily bent.

Figure 4:
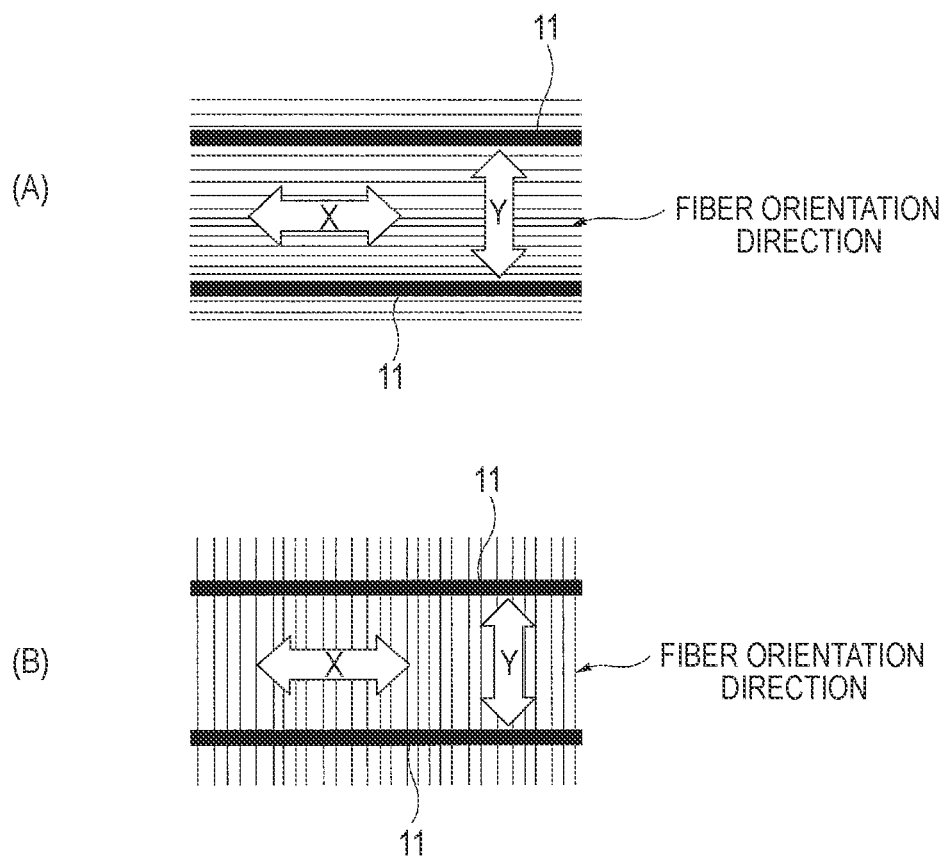
FIG. 4 is a plan view illustrating a fiber orientation direction of a front surface sheet 3 and a stretching direction of the debossed grooves 11.

Next, a description will be given of a relationship between a fiber orientation direction of the front surface sheet 3 and a stretching direction of the debossed grooves 11 with reference to FIG. 4. The fiber orientation direction of the front surface sheet 3 is a direction that coincides with a flow direction of a product when the front surface sheet 3 is manufactured, and is a direction corresponding to a winding direction of an original roll of the front surface sheet 3. That is, in a process of manufacturing the underarm sweat pad 1, the relationship between the fiber orientation direction of the front surface sheet 3 and the stretching direction of the debossed grooves 11 differs depending on whether the underarm sweat pad 1 is oriented vertically or horizontally with respect to a flow direction of a production line. In FIG. 4, the fiber orientation direction of the front surface sheet 3 is represented by a plurality of straight lines, and a direction in which these straight lines extend is the fiber orientation direction.

As illustrated in FIG. 4(A), when the direction in which the debossed grooves 11 extend substantially coincides with the fiber orientation direction of the front surface sheet 3, tearing of the front surface sheet 3 can be prevented irrespective of whether the direction of rubbing against the skin surface is a direction parallel to the debossed grooves 11 (X direction) or a direction orthogonal thereto (Y direction), and thus this mode is preferable. Specifically, when rubbing against the skin surface occurs in the direction parallel to the stretching direction of the debossed grooves 11 (X direction), an influence of restraint by the debossed grooves 11 is small, and thus a distance in which the front surface sheet 3 moves due to rubbing is large. However, since the direction is parallel to the fiber orientation direction of the front surface sheet 3, and the front surface sheet 3 itself has strength, the front surface sheet 3 is less likely to be torn. In addition, when rubbing against the skin surface occurs in a direction orthogonal to the stretching direction of the debossed grooves 11 (Y direction), since the direction is orthogonal to the fiber orientation direction, the strength of the front surface sheet 3 is weak. However, since the distance in which the front surface sheet 3 moves by rubbing is restricted by the debossed grooves 11 and narrow, the front surface sheet 3 is less likely to be torn.

On the other hand, as illustrated in FIG. 4(B), when the direction in which the debossed grooves 11 extend is substantially orthogonal to the fiber orientation direction of the front surface sheet 3, tearing is likely to occur in a direction of rubbing against the skin surface parallel to the debossed grooves 11 (direction orthogonal to the fiber orientation direction, X direction), and thus this mode is less preferable. Specifically, when rubbing against the skin surface occurs in the direction parallel to the stretching direction of the debossed grooves 11 (X direction), since this direction is a direction orthogonal to the fiber orientation direction, the strength of the front surface sheet 3 is weak. Further, since the influence of restraint by the debossed grooves 11 is small, the distance in which the front surface sheet 3 moves by rubbing increases, and the front surface sheet 3 is likely to be torn. On the other hand, when rubbing against the skin surface occurs in the direction orthogonal to the stretching direction of the debossed grooves 11 (Y direction), in addition to the fact that the direction is parallel to the fiber orientation direction and the strength is present, the influence of restraint by the debossed grooves 11 is large, the distance in which the front surface sheet 3 moves is narrow, and thus the front surface sheet 3 is less likely to be torn.

Figure 5:
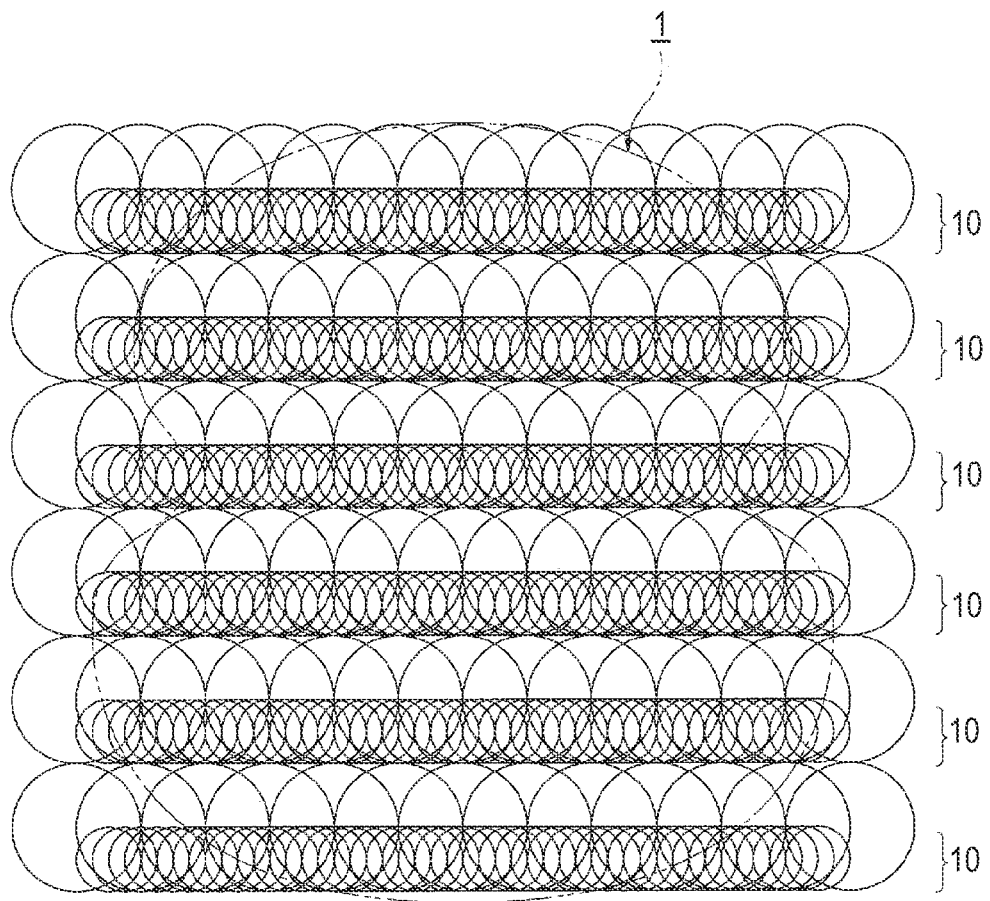
FIG. 5 is a plan view illustrating an application pattern of adhesive regions 10.

Next, a detailed description will be given of an application pattern of the adhesive in the adhesive regions 10. As the application pattern of the adhesive applied to the adhesive regions 10, it is possible to widely adopt known application methods such as spiral application, spray application, and roll application. The application pattern of the adhesive in the adhesive regions 10 may include not only a pattern in which the adhesive is applied to the entire surface of the adhesive regions 10 but also an intermittent pattern in which an application part and a non-application part of the adhesive are mixed. In FIG. 5, the adhesive is applied by spiral application.

In addition, the adhesive may not be applied to a region other than the adhesive regions 10. However, to increase the bonding strength of the front surface sheet 3, as illustrated in FIG. 5, it is preferable to apply the adhesive with a lower basis weight than that of the adhesive regions 10.

Specifically, the basis weight of the adhesive applied to the region other than the adhesive regions 10 may be set to 0 to 0.5 times, preferably about 0.2 times the basis weight of the adhesive applied to the adhesive regions 10. The basis weight of the adhesive is an average basis weight in the respective regions. The basis weight of the adhesive can be measured by a known method. For example, the basis weight can be measured by the following method described in paragraph [0042] of Japanese Patent No. 5466328. A test piece to be measured is prepared, and the area of the hot melt adhesive applied to the test piece is calculated. Then, the weight of the test piece is measured. This weight is set to x. Then, the test piece is immersed in a toluene solution to dissolve the hot melt. After dissolution, the test piece is dried and weighed. The weight is set to y. The weight of the hot melt adhesive is calculated by subtracting the weighty from the weight x. Based on the calculated hot melt weight and the area of the hot melt adhesive applied to the test piece, the basis weight of the hot melt adhesive in terms of 1 $m^2$ is calculated.

It is preferable that the pattern of the adhesive applied to the region other than the adhesive regions 10 is set to a pattern in which an application part and a non-application part are mixed (spiral application in FIG. 5) rather than solid application. In this way, it is possible to ensure liquid permeability and air permeability in this region.

OTHER EMBODIMENTS

Figure 6:
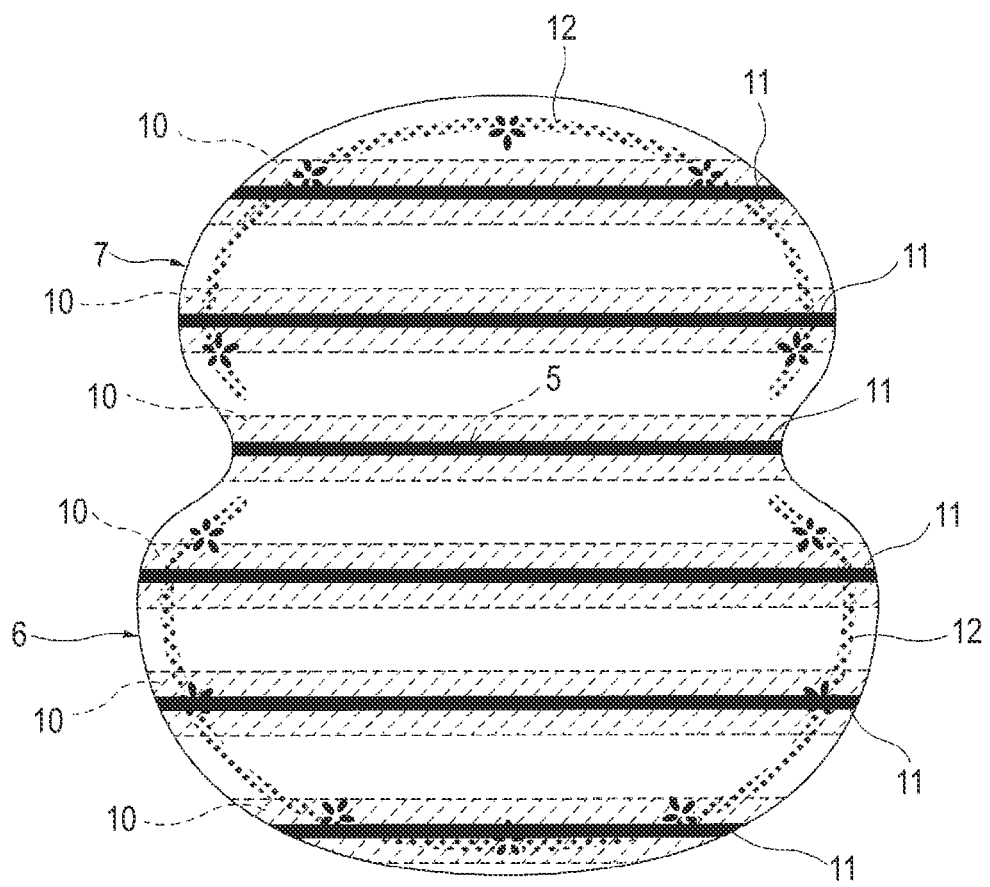
FIG. 6 is a plan view of an underarm sweat pad 1 according to a modification.

In the underarm sweat pad 1, as illustrated in FIG. 6, an outer peripheral embossed portion 12 recessed to the non-skin side may be formed on the skin-side surface of the front surface sheet 3 along a circumferential direction at inner positions of the outlines of the torso-side region 6 and the sleeve-side region 7. The outer peripheral embossed portion 12 can be provided to overlap the debossed grooves 11 at portions intersecting the debossed grooves 11. By providing the outer peripheral embossed portion 12, it is possible to prevent the front surface sheet 3 and the absorbent body 4 from being peeled off by peripheral edges of the torso-side region 6 and the sleeve-side region 7 rubbing against the skin surface or garment. Note that it is preferable that the outer peripheral embossed portion 12 is not provided at the folding line 5 and the vicinity thereof, preferably within a range of the adhesive region 10 formed at a position overlapping the folding line 5 to facilitate bending the outer peripheral embossed portion 12 at the folding line 5.

The invention claimed is:

1. An underarm sweat pad comprising:
   an absorbent body being interposed between a liquid-permeable front surface sheet and a liquid-impermeable back surface sheet, the underarm sweat pad configured to be attached to an inner side of an axillary portion of a garment and used while being bent in two parts at a folding axis,
      wherein the front surface sheet is made of a hydrophilic cellulosic fiber, and a plurality of adhesive regions in which an adhesive for bonding the front surface sheet to the absorbent body is formed as stripes that are parallel to the folding axis and are spaced at intervals in a direction orthogonal to the folding axis, and a plurality of debossed grooves recessed towards the back surface sheet is formed on an exterior surface of the front surface sheet, along a direction in which the adhesive regions extend, each debossed groove of the plurality of debossed grooves being contained entirely within, with respect to the direction orthogonal to the folding axis, each adhesive region of the plurality of adhesive regions.

2. The underarm sweat pad according to claim 1, wherein an adhesive region of the plurality of adhesive regions is formed along the folding axis at a position overlapping the folding axis, and other adhesive regions of the plurality of adhesive regions are formed to be parallel to the folding axis at intervals using the folding axis as a reference line in each of regions on both sides of the folding axis.

3. The underarm sweat pad according to claim 2, wherein a width of an adhesive region of the plurality of adhesive regions is formed to be 2 to 5 times a groove width of a debossed groove of the plurality of debossed grooves, the debossed groove overlapping the adhesive region.

4. The underarm sweat pad according to claim 2, wherein an interval between adjacent adhesive regions of the plurality of adhesive regions is 0.8 to 1.5 times the width of an adhesive region of the plurality of adhesive regions.

5. The underarm sweat pad according to claim 2, wherein one or more additional debossed grooves are formed in a linear shape along the folding axis at a position of the folding axis.

6. The underarm sweat pad according to claim 2, wherein the debossed grooves formed in adhesive regions of the plurality of adhesive regions that are located on both sides of the folding axis are formed in a straight line shape or a wavy shape in which concaves and convexes are repeated within a width of an adhesive region of the plurality of adhesive regions.

7. The underarm sweat pad according to claim 2, wherein the debossed grooves extend in a direction substantially coinciding with a fiber orientation direction of the front surface sheet.

8. The underarm sweat pad according to claim 1, wherein a width of an adhesive region of the plurality of adhesive regions is formed to be 2 to 5 times a groove width of a debossed groove of the plurality of debossed grooves, the debossed groove overlapping the adhesive region.

9. The underarm sweat pad according to claim 8, wherein an interval between adjacent adhesive regions of the plurality of adhesive regions is 0.8 to 1.5 times the width of an adhesive region of the plurality of adhesive regions.

10. The underarm sweat pad according to claim 8, wherein one or more additional debossed grooves are formed in a linear shape along the folding axis at a position of the folding axis.

11. The underarm sweat pad according to claim 8, wherein the debossed grooves formed in adhesive regions of the plurality of adhesive regions that are located on both sides of the folding axis are formed in a straight line shape or a wavy shape in which concaves and convexes are repeated within a width of an adhesive region of the plurality of adhesive regions.

12. The underarm sweat pad according to claim 1, wherein an interval between adjacent adhesive regions of the plurality of adhesive regions is 0.8 to 1.5 times the width of an adhesive region of the plurality of adhesive regions.

13. The underarm sweat pad according to claim 12, wherein one or more additional debossed grooves are formed in a linear shape along the folding axis at a position of the folding axis.

14. The underarm sweat pad according to claim 12, wherein the debossed grooves formed in adhesive regions of the plurality of adhesive regions that are located on both sides of the folding axis are formed in a straight line shape or a wavy shape in which concaves and convexes are repeated within a width of an adhesive region of the plurality of adhesive regions.

15. The underarm sweat pad according to claim 1, wherein one or more additional debossed grooves are formed in a linear shape along the folding axis at a position of the folding axis.

16. The underarm sweat pad according to claim 15, wherein the debossed grooves formed in adhesive regions of the plurality of adhesive regions that are located on both sides of the folding axis are formed in a straight line shape or a wavy shape in which concaves and convexes are repeated within a width of an adhesive region of the plurality of adhesive regions.

17. The underarm sweat pad according to claim 1, wherein the debossed grooves formed in adhesive regions of the plurality of adhesive regions that are located on both sides of the folding axis are formed in a straight line shape or a wavy shape in which concaves and convexes are repeated within a width of an adhesive region of the plurality of adhesive regions.

18. The underarm sweat pad according to claim 1, wherein the debossed grooves extend in a direction substantially coinciding with a fiber orientation direction of the front surface sheet.

19. The underarm sweat pad according to claim 1, wherein the adhesive is not applied to a region other than the adhesive regions, or is applied to the region other than the adhesive regions with a lower basis weight than a basis weight of the adhesive applied to the adhesive regions.

20. The underarm sweat pad according to claim 19, wherein the basis weight of the adhesive applied to the region other than the adhesive regions is 0 to 0.5 times the basis weight of the adhesive applied to the adhesive regions.

* * * * *